United States Patent [19]

Moller

[11] Patent Number: 5,118,338

[45] Date of Patent: Jun. 2, 1992

[54] HERBICIDAL FORMULATION CONTAINING GLYPHOSATE ACID

[75] Inventor: Jens C. Moller, Lemvig, Denmark

[73] Assignee: Cheminova Agro A/S, Lemvig, Denmark

[21] Appl. No.: 488,245

[22] Filed: Mar. 5, 1990

[30] Foreign Application Priority Data

Dec. 20, 1989 [DK] Denmark .................... 6490/89

[51] Int. Cl.⁵ .................................. A01N 57/04
[52] U.S. Cl. ........................ 71/86; 71/DIG. 1; 71/61; 71/63
[58] Field of Search ............................ 71/86

[56] References Cited

U.S. PATENT DOCUMENTS

| | | | |
|---|---|---|---|
| 3,224,865 | 12/1965 | Carlson | 71/115 |
| 3,245,775 | 4/1966 | Pfeiffer | 71/113 |
| 3,799,758 | 3/1974 | Franz | 71/86 |
| 3,977,860 | 8/1976 | Franz | 71/86 |
| 4,025,332 | 5/1977 | Franz | 71/86 |
| 4,486,358 | 12/1984 | Moser | 71/86 |
| 4,931,080 | 6/1990 | Chan et al. | 71/87 |

FOREIGN PATENT DOCUMENTS

| | | |
|---|---|---|
| 2348 | 9/1988 | Denmark . |
| 0206537 | 12/1986 | European Pat. Off. . |
| 0274369 | 7/1988 | European Pat. Off. . |
| 0290416 | 11/1988 | European Pat. Off. . |
| 2098482 | 11/1982 | United Kingdom . |

OTHER PUBLICATIONS

Research Disclosure Dr. Bakel, 27161, "Novel Glyphosate acid wettable powder . . . " Nov. 1986, p. 693.

"The Herbicide Glyphosate", Ed. E. Grossbard et al., Butterworths & Co., 1985, pp. 3-4.
1985 BCPC Monogram No. 28, Symposium on Application and Biology, "Studies with Alternative Glyphosate", D. J. Turner, pp. 135-143.
"Concise Chemical and Technical Dictionary", 3rd Enlarged Ed., Chemical Publishing Co., Inc., New York (1974), pp. 939-940.
Collins Dictionary of the English Language, William Collins Sons & Co., Ltd., 1979, p. 910.
Webster's Third New International Dictionary of the English Language, Unabridged, Merriam-Webster Inc., 1986, p. 1393.
Encyclopedia of Chemical Technology, Third Edition, John Wiley & Sons, 1979, vol. 6, "Chocolate and Cocoa to Copper", pp. 697-699.
Encyclopedia of Chemical Technology, Third Edition, John Wiley & Sons, 1979, vol. 15, "Matches to N-Nitrosamines", pp. 483-484.

Primary Examiner—Richard L. Raymond
Assistant Examiner—B. Bembenick
Attorney, Agent, or Firm—Wegner, Cantor, Mueller & Player

[57] ABSTRACT

A herbicidal formulation which is a water-soluble powdery or granular free-flowing formulation comprising glyphosate acid (N-phosphonomethylglycine) and a surface-active agent that is a powdery or granular nonionic polyglycol ether of a straight chain, saturated, high molecular weight fatty alcohol having an average chain length of $C_{16}$-$C_{18}$, about 25 units of ethylene oxide per mole of fatty alcohol and an HLB value of about 16, said formulation is a highly efficient herbicide.

4 Claims, No Drawings

HERBICIDAL FORMULATION CONTAINING GLYPHOSATE ACID

BACKGROUND OF THE INVENTION

1. Field of the Invention

This invention relates to a new, water-soluble, high concentrated and efficient, powdery or granular herbicidal formulation comprising so-called glyphosate in free acid form.

2. Description of the Prior Art

Glyphosate acid, which is also designated N-phosphonomethylglycine $(HOOCCH_2NHCH_2PO(OH)_2)$, and especially salts of said acid are known as an effective total post-emergent herbicide such as will appear from the book "The Herbicide Glyphosate" by E. Grossbard and D. Atkinson, Butterworth & Co. Ltd., 1985, ISBN 0-408-11153-4.

Several processes for the preparation of glyphosate are described in the literature, e.g., in U.S. Pat. Nos. 3,977,860 and 4,486,358. Normally the glyphosate is isolated as the free acid, the easiest way to isolate the pure product.

In the following a clear distinction should be made between the glyphosate free acid, the formulation of which is the subject of the present invention, and glyphosate salts, the formulation of which is the subject of most other inventions in this field.

The known marketed formulations contain glyphosate salts and most commonly the isopropylamine salt. A conventional formulation is known under the name of Roundup.

Patent publications dealing with such formulations are U.S. Pat. Nos. 4,405,531 and 3,799,758, EP Published Specification No. 274,369, the Specification of Danish Patent Application No. 2348/88 and GB Published Specification No. 2,098,481.

Said types of formulations are not to be discussed in more detail since they are outside the scope of the present invention.

Further to be mentioned is a "formulation of glyphosate acid" which is mentioned in BCPC Monogram No. 28 from 1985 by D. J. Turner and P. M. Tabbush. A closer study of same shows, however, that it does not concern an acid, formulation, as the acid by heating at 100° C. for one hour, reacts with an excess of a fatty amine in water, and the glyphosate acid is thereby converted to a salt.

EP Patent Specification No. 206,537 also describes a solid, including a powdery or granular formulation of glyphosate derivatives. Said formulation is prepared by melting a surface-active agent, and the glyphosate compound is added in a concentrated solution by means of a solvent. Afterwards the solvent is then removed. However, in said patent specification no examples are mentioned where the glyphosate is used as the free acid, and this is understandable as the solubility of the free acid is so low that the process according to EP Patent Specification No. 206,537 is inapplicable to a free acid formulation.

In Research Disclosure, November 1986, 27161, a wettable powder formulation of glyphosate acid is described; however, as it clearly appears said formulation is not a water-soluble formulation and thus is outside the scope of the present invention as will appear from the following.

The above publications are herein incorporated by reference.

The fact is that it has now surprisingly been found that a simple combination of a certain powdery surface-active agent and the glyphosate acid provides a water-soluble free-flowing formulation having a herbicidal activity that is better than or at least as good as the activity of Roundup and having a substantially better cost-efficiency ratio.

SUMMARY OF THE INVENTION

Various studies have been directed towards developing a formulation of glyphosate which contains the free glyphosate acid and which retains its chemical and physical properties for an extended period of time and is able to exhibit a herbicidal effect comparable to or better than the above-mentioned conventional formulations but which, unlike the conventional formulations, does not contain a salt of the glyphosate acid and does not contain large amounts of water. As a result of these studies, the present inventor has found that the free acid of glyphosate mixed with a surface-active agent like a nonionic polyglycol ether of a fatty alcohol and, if desired, complexing and penetrating agents and the like is an extremely effective formulation having the desired properties.

Accordingly, it is a principal object of the present invention to provide a herbicidally active powdery or granular formulation of the free acid of glyphosate which retains its chemical and physical properties for an extended period of time.

More particularly, it is an object of the present invention to provide a herbicidally active formulation which is free from the drawbacks which accompany the conventional production and handling of formulations of salts of glyphosate.

It is another object of the present invention to provide a herbicidally active formulation which is a free-flowing and water-soluble formulation of the free acid of glyphosate.

DETAILED DESCRIPTION OF THE INVENTION

A formulation that meets the requirements described above can be economically prepared by a simple method which comprises mixing by mechanical means the fine particles of the free acid of glyphosate, the surface-active agent and, if desired, complexing and penetrating agents and the like.

A brief description of the formulation of this invention will be given below. The formulation of the present invention comprises essentially the following ingredients:

N-phosphonomethylglycine.

Powdery or granular surface-active ingredient.

The choice of surface-active ingredient is very important. The surface-active ingredient must be a solid at ambient temperatures, which means that it must have a high melting point. Further it must not be waxy, but instead appear as a dry free-flowing powder or granulate.

The special surface-active ingredient to be used in the formulation of the invention is a nonionic polyglycol ether of a straight chain, saturated, high molecular weight, ethoxylated fatty alcohol having an average chain length of $C_{16}$ - $C_{18}$, about 25 units of ethylene oxide per mole of fatty alcohol and an HLB value of about 16. An example of such a surface-active agent is known under the brand name Genapol T 250.

Those skilled in the art will appreciate that other surface-active agents lying within the scope of the invention may also be suitable.

Furthermore, various water-soluble additives in the form of powders or granules may of course be added without changing the nature of the present invention.

Other additives in the form of liquids may be added in minor amounts as long as they are not changing the physical free-flowing character of the formulation.

Additives can be complexing agents, penetrating agents, surface tension and contact angle reducing agents, humidifying agents and anti-foaming agents.

Complexing agents suitable in the formulation of the invention are commercially available products. Suitable complexing agents are ammonium sulfate, sodium sulfate, trisodium phosphate, nitrilotriacetic acid trisodium salt, ethylenediaminetetraacetic acid, citric acid, malic acid, ammonium phosphate and diammonium hydrogen orthophosphate.

Penetrating agents suitable in the formulation of the present invention are commercially available products. Suitable penetrating agents that by an accelerated plant cell activity aid the penetration into the vascular systems of the plants are ammonium sulfate, ammonium phosphate, ammoniumtri(methylene)-phosphonic acid, diammonium hydrogen phosphate, ammonium carbonate, ammonium acetate, triammonium phosphate, ammonium hydrogen carbonate, urea, ammonium hydrogen sulfate, and ammonium dihydrogen phosphate.

Surface tension and contact angle reducing agents suitable in the formulation of the present invention are commercially available products. Suitable surface tension and contact angle reducing agents are, e.g., organosilicones, polyoxy ethanol esters and various surfactants.

Humidifying agents suitable in the formulation of the present invention are commercially available products. Suitable humidifying agents are hexylene glycol, glycerol, sodium carboxymethyl cellulose, polyvinylpyrrolidone, natural gums, alginates and polyacrylamide.

Anti-foaming agents suitable in the formulation of the present invention are commercially available products. Suitable anti-foaming agents are, e.g., dimethylpolysiloxanes.

The mention of the above products excludes in no way the use of other products with same effects according to this invention.

In addition to the demonstrated surprising improvement as to herbicidal effect achieved by the formulation of the present invention, there are other considerable advantages connected to the invention.

In comparison to formulations based on salts dissolved in water, the acid formulation of the present invention has the particular advantage of being a simple process of dry mixing the ingredients, in contrast to the dissolution process of conventional formulations. Furthermore, excluding water from the formulation contributes to a better economy with respect to container and storage costs. In comparison the known water-dissolved salt formulations like Roundup consist of about 50 percent of water.

Compared to the acid formulation known from the literature, the formulation of the present invention does not contain ingredients that are insoluble in water. Consequently there will be no clogging of the application equipment during application and furthermore the applicator is able to evaluate with ease when the powder is dissolved in the spraying tank and the tank mixture therefore ready for use.

Suspension concentrates also contain considerable amounts of water and therefore will not be stable against freezing. The powdery or granular formulation of the invention is inherently freeze-stable.

In addition the powdery or granular formulation of the invention is very easy to collect in case of undeliberate spills of concentrate and in that way becomes environmentally more safe.

The present invention consequently implies great advantages in preparing as well as in handling and use of the glyphosate acid formulation.

The ratios of the glyphosate acid to the surface-active agent in the formulation of the invention may be widely varied. The amount of surface-active agent can have an important influence on the efficacy of the glyphosate acid, and the ratio of the glyphosate acid to the surface-active agent may be chosen as required. The ratio of the glyphosate acid to the surface-active agent will typically be from about 6:1 to about 1:6.

The preferred ratio will be from about 2:1 to about 1:2.

Representative Examples of the formulation of the invention are given below, the percentages being by weight.

| Example 1 | |
|---|---|
| Glyphosate acid: | 35% |
| Genapol T 250: | 65% |
| Total | 100% |
| Example 2 | |
| Glyphosate acid: | 65% |
| Genapol T 250: | 35% |
| Total | 100% |

The amount of formulation to be used per hectare depends on the nature of the plant, the microclimate and the intended degree of efficacy. Normally the rate will vary between 0.1 and 10 kg per hectare.

The following Examples demonstrate the efficacy of formulations according to the present invention. The efficacy is compared with that of Roundup and the tests have been carried out in two different test systems:

| TEST SYSTEM 1 | | |
|---|---|---|
| Formulation | Rate in grams of a.i. per unit area | Efficacy on *Hordeum vulgare* % kill |
| Roundup | 20 | 4 |
|  | 60 | 10 |
|  | 180 | 60 |
|  | 540 | 100 |
| Glyphosate acid | 20 | 11 |
| Genapol T 250 | 60 | 26 |
|  | 180 | 80 |
|  | 540 | 100 |
| Glyphosate acid | 20 | 24 |
| Genapol T 250 | 60 | 54 |
| Ammonium sulfate | 180 | 84 |
|  | 540 | 100 |
| Glyphosate acid | 20 | 20 |
| Genapol T 250 | 60 | 61 |
| Ammonium sulfate | 180 | 94 |
| Complexing agent | 540 | 100 |
| Glyphosate acid | 20 | 24 |
| Genapol T 250 | 60 | 52 |
| Ammonium sulfate | 180 | 86 |
| Surface tension reducing agent | 540 | 100 |

-continued

| TEST SYSTEM 1 | | |
| --- | --- | --- |
| Formulation | Rate in grams of a.i. per unit area | Efficacy on Hordeum vulgare % kill |
| Glyphosate acid | 20 | 24 |
| Genapol T 250 | 60 | 48 |
| Ammonium sulfate | 180 | 88 |
| Complexing agent | 540 | 100 |
| Surface tension reducing agent | | |
| Anti-foaming agent | | |

Roundup is the brand name of Monsanto's commercial glyphosate salt formulation.

| TEST SYSTEM 2 | | | |
| --- | --- | --- | --- |
| | | Elymus repens | |
| Formulation | Rate in grams of a.i. per unit area | Dry weight at harvest in gr/plot | % Regrowth |
| Roundup | 25 | 6.0 | 39.0 |
| | 50 | 4.5 | 15.1 |
| | 100 | 3.6 | 4.7 |
| Glyphosate acid | 25 | 4.4 | 13.3 |
| Genapol T 250 | 50 | 2.9 | 6.2 |
| Ammonium sulfate | 100 | 1.7 | 1.7 |
| Complexing agent | | | |

Although this invention has been described with reference to specific embodiments, the details thereof are not to be construed as limiting, as it is obvious that one can use various equivalents, changes and modifications and still be within the scope of the present invention.

What is claimed is:

1. A herbicidal formulation, characterized by being a water-soluble powdery or granular free-flowing formulation, comprising a mixture of:
   a herbicidally effective amount of the glyphosate acid N-phosphonomethylglycine; and
   a surface-active agent that is a powdery or granular nonionic polyglycol ether of a straight chain, saturated, high molecular weight fatty alcohol having an average chain length of $C_{16}$-$C_{18}$, about 25 units of ethylene oxide per mole of fatty alcohol and an HLB-value of about 16,
   wherein the ratio of the glyphosate acid to the surface active agent is from about 6:1 to 1:6.

2. The formulation in accordance with claim 1, further comprising a powdery or granular ammonium sulfate.

3. The formulation in accordance with claim 1, further comprising a complexing agent.

4. The formulation in accordance with claim 1, wherein the ratio of the glyphosate acid to the surface active agent is from about 2:1 to about 1:2.

* * * * *

UNITED STATES PATENT AND TRADEMARK OFFICE
CERTIFICATE OF CORRECTION

PATENT NO. : 5,118,338
DATED : June 2, 1992
INVENTOR(S) : Jens Christian MØLLER

It is certified that error appears in the above-identified patent and that said Letters Patent is hereby corrected as shown below:

On the title page item [56], entitled "Foreign Patent Documents," the last document recorded, please change "2098482" to --2098481--.

Column 1, line 46, please delete the first comma, and after "acid" (Second occurrence) add a comma.
Column 6,
Claim 1, last line, change "from about 6:1 to 1:6" to --from about 6:1 to about 1:6--.

Signed and Sealed this

Twenty-fourth Day of August, 1993

Attest:

BRUCE LEHMAN

*Attesting Officer*  *Commissioner of Patents and Trademarks*